United States Patent [19]

Roberts

[11] Patent Number: 5,168,059
[45] Date of Patent: Dec. 1, 1992

[54] MICROPROPAGATION PROCESS

[75] Inventor: Andrew V. Roberts, Epping, England

[73] Assignee: Imperial Chemical Industries PLC, London, England

[21] Appl. No.: 65,032

[22] Filed: Jun. 19, 1987

[30] Foreign Application Priority Data

Jul. 9, 1986 [GB] United Kingdom ............... 8616685

[51] Int. Cl.$^5$ ............................................ C12N 5/00
[52] U.S. Cl. .......................... 435/240.45; 435/240.54
[58] Field of Search ................. 71/92, 94; 435/240.54, 435/240.45

[56] References Cited

PUBLICATIONS

Chin (1982) Hort Science 17(4): 590–591.
Plant Growth Regulation 3:37–45 (1985) Copyright 1985, Martinus Niihoff/Dr. W. Junk Publishers, Dordrecht, Netherlands, "The Effects of (2RS,3RS) . . . ", Asamoah et al.
Asare-Boamah, Hofstra, Fletcher and Dumbroff; *Plant Cell Physiol.* 27(3); 383–390 (1986).
Fletcher and Hofstra, *Plant Cell Physiol.* 26(4); 775–780 (1985).
Chien Yi Wang, *Scientia Horticulturae* 26 (1985) 293–298.
Wardle and Short (*Biochem. Physio. Pflanzen,* 178:619–624 (1983).
Dalziel et al., "Biochemical and Biological Effects of Kaurene Oxidase Inhibitors, Such as Paclobutrazol", British Plant Growth Regulator Group, Monograph 11 (1984).
Wardle Dobbs and Short, "In Vitro Acclimatization of Aseptically Cultured Plantlets to Humidity", *J. Am. Soc. Hort. Sci.,* 108(3) May 1983.
Sorbarod Sytems; Publicity Brochure.
Sorbarods in Micropropagation Data Sheets.
Menhenett "Comparison of a New Triazole Retardant, etc.", *Scientia Hort.,* 24:349–358 (1984).
Wardle et al., "Redistribution of Rubidium in Plants, etc.", *Ann Bot.,* 261–264 (1983).
Tweddle et al., "In Vitro Culture of Roses", *Int. Symp. Plant Tissue and Cell Culture Czechoslavakia* (1984).

*Primary Examiner*—David T. Fox
*Attorney, Agent, or Firm*—Cushman, Darby & Cushman

[57] ABSTRACT

The present invention provides a process for improving the viability of plantlets on transfer from in vitro micropropagation conditions to in vitro conditions which comprises incorporating in the in vitro medium from 0.001 to 10 mg of a plant growth regulator per liter of in vitro medium wherein the plant growth regulator is an inhibitor of the gibberellin pathway.

7 Claims, No Drawings

MICROPROPAGATION PROCESS

This invention relates to a micropropagation process and in particular to a process for improving the viability of plants on transfer from in vitro micropropagation conditions to in vivo conditions.

The micropropagation of plants using tissue culture techniques for the in vitro production of plantlets is now well established. However, in vitro cultured plantlets often exhibit poor water relations when transferred to in vivo soil conditions and one major cause of plantlet loss on transplanting is desiccation. In commercial practice, expensive mist propagators may be used to maintain plantlets transplanted from in vitro culture media under carefully controlled conditions of humidity and temperature prior to planting out in field conditions. However, even using these techniques, the rate of plant loss is often high.

A number of studies have suggested that conventional micropropagation techniques result in abnormal stomatal physiology including large stomatal apertures and guard cells which are unable to close completely. The conditions of high humidity under which the plantlets are grown in also believed to be the cause of greatly reduced epicuticular wax formation which adds to uncontrolled foliar water loss and consequent desiccation. A number of attempts have been made to reduce transpiration of plantlets grown by micropropagation techniques. For example Wardle and Short (Biochem. Physio. Pflanzen 178, 619-624 (1983)) were able to induce wax development and the formation of stomata with narrow apertures by culturing chrysanthemum plantlets in vitro under conditions of low humidity. However, the beneficial effect observed on the rate of water loss was offset by the deleterious effect on plantlet growth. The same paper reports the investigation of the effect on the incubation of abaxial epidermal strips of chrysanthemum plantlets of the addition the naturally occurring plant growth hormone ABA and its precursor, farnesol. The addition of the cytokinin, kinetin, was also investigated. However, no improvement was observed and it was concluded that further opening of the stomata was possible (using carbon dioxide-free air with kinetin), whereas closure was not possible (for example using darkness and ABA) even after extended incubation periods. Closure was observed using farnesol but this was presumed to be due to its known ability to disrupt membranes.

We have now found that, surprisingly, certain plant growth regulators may be used to improve the viability of plants on transfer from in vitro micropropagation conditions to in vivo conditions.

Thus according to the present invention there is provided a process for improving the viability of plantlets on transfer from in vitro micropropagation conditions to in vivo conditions which comprises incorporating in the in vitro medium form 0.001 to 10 mg of a plant growth regulator per liter of in vitro medium wherein the plant growth regulator is an inhibitor of the gibberellin pathway.

The classification of a plant growth regulator as an inhibitor of the gibberellin pathway may be readily undertaken by those skilled in the art using established procedures. For example, inhibition of the gibberellin biosynthesis pathway may be demonstrated in the fungal system *Gibberella fujikuori* using the techniques described in British Plant Growth Regulator Group, Monograph 11-1984, discussed below.

An especially preferred class of gibberellin pathway inhibitors are those which function as kaurene oxidase inhibitors, for example 1-(4-chlorophenyl)-4,4-dimethyl-2-(1H-1,2,4-triazol-1-yl)pentan-3-ol and stereoisomers thereof. A typical experimental procedure for determining whether a plant growth regulator is a kaurene oxidase inhibitor is described for example in the paper "BIOCHEMICAL AND BIOLOGICAL EFFECTS OF KAURENE OXIDASE INHIBITORS, SUCH AS PACLOBUTRAZOL (British Plant Growth Regulator Group, Monograph 11-1984, J Dalziel and D K Lawrence).

Thus according to a further aspect of the present invention there is provided a process for improving the viability of plantlets on transfer from in vitro micropropagation conditions to in vivo conditions which comprises incorporating in the in vitro medium from 0.001 to 10 mg of plant growth regulator per liter of in vitro medium wherein the plant growth regulator is 1-(4-chlorophenyl)-4,4-dimethyl-2-(1H-1,2,4-triazol-1-yl)pentan-3-ol and stereoisomers thereof.

An especially suitable plant growth regulator is paclobutrazol, (2RS, 3RS)-1-(4-chlorophenyl)-4,4-dimethyl-2-(1H-1,2,4-triazol-1-yl)pentan-3-ol.

Preferably there is applied to the in vitro medium from 0.05 to 5, and especially from 0.1 to 1, for example from 0.3 to 1, mg of plant growth regulator (for example paclobutrazol) per litre of in vitro medium.

The in vitro medium may be a conventional gel culture medium such as a culture medium containing suitable nutrients and solidified using, for example agar. A typical formulation of such a culture medium contains for example salts, nutrients and vitamins such as those described by Murashige and Skoog (A revised medium for rapid growth and bioassays with tobacco tissue cultures (Physiol Plant 15 473-497 (1962)) Supplements the medium may also be used, and as examples of suitable supplements there may be mentioned benzylaminopurine and naphthaleneacetic acid. It is to be understood that such salts, nutrients, vitamins and supplements are not to be considered "plant growth regulators" as that term is used herein.

Plantlets grown (in vitro) by micropropagation techniques in such a gel culture medium may be transferred (transplanted) directly into a suitable (in vivo) micropropagation soil medium housed in a suitable container and maintained under controlled conditions of humidity and temperature before being planted on.

Preferably however, the in vitro medium from which the plantlets are transferred into a suitable (in vivo) soil medium is a liquid medium. For example a plantlet may be divided by conventional micropropagation techniques and the propagated portions (for example a terminal bud, axillary shoot or nodal section) may be placed on a suitable solid porous carrier housed in vitro in a suitable liquid medium. It will be appreciated that the original plantlet used as the source for the micropropagation may itself have been grown in a gel multiplication medium, and that the gel medium may, but need not, contain a plant growth regulator.

Thus according to a still further aspect of the present invention, there is provided a process for improving the viability of plantlets on transfer from in vitro micropropagation conditions to in vivo conditions which comprises culturing the plantlets in contact with a solid porous carrier housed in vitro in a liquid in vitro culture medium wherein there is incorporated in the in vitro medium from 0.001 to 10 mg of a plant growth regulator per litre of in vitro medium and wherein the plant growth regulator is an inhibitor of the gibberellin pathway.

The solid porous carrier allows the ready access of the liquid medium to the plantlet through capillary action and permits the development of a root system within the carrier. Thus it is generally sufficient to stand the solid porous carrier in the liquid medium rather than to immerse it fully. When the plantlet is ready to be transferred into an in vivo soil medium, the entire solid carrier may be transplanted without the necessity of disturbing the root system. The solid carrier is preferably a plug of a fibrous material, such as cellulose, which is preferably biodegradable and which can be readily sterilized, for example by treatment in an autoclave or by irradiation. Cellulose plugs suitable for this purpose are commercially available under the trade name "Sorbarod".

The use of a plant growth regulating agent according to the present invention renders the plantlets more viable on transfer from the in vitro, micropropagation conditions (for example contact with a liquid in vitro medium) to the in vivo soil conditions. That is to say that the plants achieve a better survival rate on transfer from in vitro conditions to in vivo conditions or that the in vivo transplants require less carefully controlled environmental conditions (such as humidity and temperature) to achieve acceptable survival rates.

It will generally be convenient to add the plant growth regulator to the freshly prepared liquid to be used as the in vitro medium and to maintain the plantlet in contact with the liquid in vitro medium containing the plant growth regulator until the plantlet is ready for transplantation into an in vivo soil medium (in general from 2 to 8 weeks depending on the species and the nature of the propagule). The plant growth regulator may however, if desired, be added to the liquid in vitro medium at an intermediate stage between the micropropagation and the eventual transfer of the plantlet in vivo.

The liquid in vivo medium may contain conventional nutrients and supplements such as those described above for gel media.

Whilst the scope of the present invention is not to be taken to be limited by any one particular theory, the plant growth regulator is believed to have a number of beneficial effects which may contribute to the improvement of the viability of plants on transfer from in vitro micropropagation conditions to in vivo conditions. In particular, the plant growth regulator may reduce the stomatal aperture and its ability to close; may produce thicker guard cell membranes; may produce better formed chloroplasts; may provide thicker cuticular wax; may stimulate root formation and favourable root habit; may have a greening effect; may provide more numerous and better developed leaf hairs; may reduce internodal length, providing a more favourable habit in the mature plant; may ensure that leaf number and size are normal; and may protect from frost damage.

The process of the present invention is generally applicable to a wide variety of plant species which are capable of propagation by micropropagation techniques. Typical species suitable for treatment in the process of the present invention include herbaceous and woody ornamental plants, herbaceous and woody crop plants, deciduous and evergreen forestry plants and plantation crops.

The invention is illustrated by the following Examples.

EXAMPLE 1

Cultures were taken from *Chrysanthemum morifolium,* 'Pennine Reel'; and *Rosa hybrida* 'Mountbatten'. To initiate cultures, explants consisting of terminal buds were surface sterilized in a solution of sodium hypochlorite (1–1.5%) to which one drop of surfactant was added. Buds were immersed in this solution for 20 minutes and were washed twice in sterile distilled water for 20 minutes before being transferred to an in vitro gel multiplication medium. The gel multiplication medium comprised the formulation of salts, nutrients and vitamins disclosed by Murashige and Skoog (Physiol. Plant 15, 473–497 (1962)) and contained 30 g per litre of sucrose. In addition the medium used for Rosa cultures contained 0.5 mg per litre benzylaminopurine and 0.005 mg per litre naphthaleneacetic acid. The medium was adjusted to pH 5.6 prior to the addition of 8 g per litre of agar and sterilized in an autoclave at 121° C. for 15 minutes.

All transfers were carried out in a laminar air-flow cabinet and instruments used in the transfer were first immersed in industrial methylated spirit and flamed. All cultures were maintained at 23±1° C. in a 16 hour photoperiod supplied by cool white fluorescent tubes giving 3 Wm$^{-2}$.

Chrysanthemum was multiplied from nodal sections and terminal buds, and subcultured every 6 weeks.

Rosa was multiplied from axillary shoots and subcultured every four weeks.

The propagated portions which had been established in the gel multiplication medium as described above were then transferred to a closed vessel where they were placed on a solid porous carrier housed in vitro in a liquid culture medium.

More specifically, "Sorbarod" plugs supplied by Baumgartner Papiers QA, Switzerland were used as solid porous carrier. The cylindrical plugs were 20 mm in height and either 18 mm or 10 mm in diameter and consisted of a packing of laminated cellulose enclosed in a perforated polypropylene or paper sleeve. The plugs were radiation sterilized by the supplier. The plugs were placed in a liquid culture medium which was the same as the gel culture medium described above except that (a) no agar was included and (b) the liquid medium contained 0.3 or 1.0 mg per litre of paclobutrazol. The liquid medium was sterilized either by autoclaving or by filtration. The volume of liquid medium used was sufficient to be absorbed by the porous plug (each of which was capable of absorbing nearly its own volume of liquid) whilst retaining a few mm depth of liquid at the base of the closed in vitro vessel. A propagule was inserted into an indentation in the top surface of each plug, and the cultures were maintained in vitro in the closed vessel for 4 weeks before transplanting. At this time the roots of each plantlet were well established in the plug, and the entire plug with the plantlet growing in it was transferred into the in vivo soil medium without disturbing the roots.

After transplanting the plants were maintained in an open laboratory environment (without a protective cover) rather than a mist propagator. The plants were assessed over a period of 2 weeks after transplanting and were compared with controls which were treated in exactly the same way except that no paclobutrazol was included in the liquid culture medium.

As compared with the untreated plants, the plants treated with paclobutrazol in the liquid medium clearly showed a greater viability. In particular they showed less wilting; deeper green coloration; greater stomatal closure; greater development of epidermal hairs; thicker and more robust leaves; and more numerous roots.

EXAMPLE 2

Chrysanthemum was multiplied from nodal sections as generally described in Example 1. The nodal sections were established on a gel multiplication medium comprising the formulation described by Murashige and Skoog with the addition of 30 g per litre of sucrose, 0.01 mg per litre of naphthaleneacetic acid, 0.1 mg per litre benzylaminopurine and 8 g per litre agar. The propagated portions were then transferred to a closed vessel where they were placed on a 18 mm diameter solid porous carrier ("Sorbarod") housed in vitro in a liquid culture medium. The liquid culture medium was as described for multiplication above except that it contained no benzylaminopurine and no agar. The culture medium also contained 1 mg of paclobutrazol per litre, added as a solution of paclobutrazol in ethanol at a rate of 0.1 ml of ethanolic solution of paclobutrazol per litre of culture medium. 30 such plantlets were grown in vitro and maintained for 4 weeks at 23° C. in a 16 hour photoperiod supplied by cool white fluorescent tubes to give 55 microEinsteins per meter$^2$ per sec.

By way of comparison, a corresponding batch of 30 plantlets was cultured under identical conditions except that the plant growth regulator was omitted from the in vitro culture medium. By way of further comparison, a corresponding batch of 30 plantlets was cultured under identical conditions except that instead of using a solid porous carrier, the culture medium was solidified using agar at a concentration of 8 g per litre of culture medium. No plant growth regulator was used.

Each batch of 30 plantlets was then transferred to in vivo conditions and planted into 3 inch pots containing Minster peat which had previously been well watered. Each pot was placed in a propagator until all thirty plants had been potted. The plantlets cultured in contact with the porous plug were planted in the peat with the top of the plug at the level of the surface of the peat in the pot. The plantlets grown in contact with a porous plug were found to be quicker and easier to handle than those grown in agar.

All three batches of plantlets were then moved from the propagator and set out in a randomised block design in a growth room maintained at 27.5° C. and 50% relative humidity under a 16 hour photoperiod provided by mercury fluorescent tubes with supplementary tungsten bulbs giving 300 μE/m$^2$/sec.

Each plant was examined after one half hour and then after 4 hours and was assessed for wilting on a score of 0 to 5 where an undamaged plant scored 0 and a completely flacid plant scored 5. The mean of these scores for all 30 plants in each batch is given in Table I.

The appearance of the plants was also observed after 1 and 2 days, and, although all the plants had partially recovered from initial wilt, those treated with the plant growth regulator during in vivo propagation still showed an improved appearance as compared with the untreated plants.

Plants were maintained for 9 days in the growth room, after which they were transferred to a glasshouse at 25° C. day and 22° C. night temperatures with supplementary sodium vapour lighting for 14 hours. Three weeks after transplantation, it was observed that those plants which had been treated with the plant growth regulator during in vitro propagation showed less damage on the lower leaves as a result of initial wilt. Several treated plants had produced side shoots, whilst in untreated plants this was rare. Chrysanthemums are a relatively hardy species. However, even under the well controlled transfer conditions of this experiment, 3 plants which were not treated with paclobutrazol during in vitro propagation failed to become established and died. There were no losses in the plants which had been treated with paclobutrazol.

TABLE I

WILTING OF MICROPROPAGATED CHRYSANTHEMUMS ON A SCORE OF 0 (UNDAMAGED) TO 5 (WHOLE PLANT FLACCID)

| In Vitro Medium | Wilting half hour after transplantation | Wilting four hours after transplantation |
|---|---|---|
| Porous carrier/ paclobutrazol | 0 | 0.2 |
| Porous carrier/ No paclobutrazol | 1.7 | 1.4 |
| Agar | 1.6 | 2.7 |

EXAMPLE 3

Nodal sections of Chrysanthemum were micropropagated using the techniques and conditions described in Example 2. In this experiment, a number of different plant growth regulators were evaluated at a concentration of 0.3, 1.0 and 3.0 mg of active ingredient per litre of in vitro medium respectively. 30 replicates were used for each concentration, and the results were compared with a further 30 replicates containing no plant growth regulator as control. Wilting was assessed 1 hour and 3 hours after transplanting, using the scale of 0 to 5 described in Example 2. The results are presented in Tables 2 and 3 in which the mean of the 30 replicates is given in each case. The plant growth regulators used were as follows :

A. Alpha-(1-methyl ethyl)-alpha-[4-(trifluoromethoxy)-phenyl]-5-pyrimidine-methanol: common name flurprimidol.

This plant growth regulator is an inhibitor of the gibberellin pathway, functioning as a kaurene oxidase inhibitor.

B. Paclobutrazol. This plant growth regulator is an inhibitor of the gibberellin pathway, functioning as a kaurene oxidase inhibitor.

C. Alpha-cyclopropyl-alpha-(4-methoxyphenyl)-5-pyrimidine-methanol: common name ancymidol. This plant growth regulator is an inhibitor of the gibberellin pathway, functioning as a kaurene oxidase inhibitor.

D. (E)-1-cyclohexyl-4,4-dimethyl-2-(1H-1,2,4-triazol-1-yl)-pent-1-en-3-ol: common name triazethan, triazethanol or triapenthenol.

This plant growth regulator is an inhibitor of the gibberellin pathway, functioning as a kaurene oxidase inhibitor.

E. E-1-(4-chlorophenyl)-4,4-dimethyl-2-(1,2,4-triazol-1-yl)pent-1-en-3-ol: common name uniconazol or fenpentazol.

This plant growth regulator is an inhibitor of the gibberellin pathway, functioning as a kaurene oxidase inhibitor.

F. Tributyl-(2,4-dichlorobenzyl)phosphonium ion (chloride): common name chlorphonium.

This plant growth regulator is an inhibitor of the gibberellin pathway, but functions in the pathway before the kaurene oxidase stage.

G. All-cis-5-(4-chlorophenyl)-3,4,5,9,10-pentaatatetracyclo-5,4,1,0$(^{2,6})$, 0$(^{8,11})$ dodeca-3,9-diene: common name tetcyclacis.

This plant growth regulator is an inhibitor of the gibberellin pathway, functioning as a kaurene oxidase inhibitor.

TABLE 2

WILTING OF TRANSPLANTED CHRYSANTHEMUMS -
1 hour after transplantation

| Plant Growth Regulator | Concentration (mg per liter) | | | |
|---|---|---|---|---|
| | 0 | 0.3 | 1 | 3 |
| A | 3.2 | 0.5 | 0.2 | 0 |
| B | 2.1 | 0.3 | 0.2 | 0.1 |
| C | 3.6 | 1.3 | 0 | 0 |
| D | 3.0 | 0.8 | 0.5 | 0 |
| E | 3.3 | 1.4 | 0.3 | 0 |
| F | 2.6 | 1.1 | 0.4 | 0 |
| G | 2.0 | 2.4 | 1.5 | 0.7 |

TABLE 3

WILTING OF TRANSPLANTED CHRYSANTHEMUMS -
3 hours after transplantation

| Plant Growth Regulator | Concentration (mg per liter) | | | |
|---|---|---|---|---|
| | 0 | 0.3 | 1 | 3 |
| A | 3.0 | 1.0 | 0.2 | 0.1 |
| B | 1.3 | 0.3 | 0.5 | 0.2 |
| C | 3.3 | 1.0 | 0.2 | 0.1 |
| D | 2.6 | 0.7 | 0.7 | 0.0 |
| E | 2.9 | 1.3 | 0.8 | 0.2 |
| F | 2.3 | 0.8 | 0.8 | 0.2 |
| G | 1.9 | 2.5 | 1.8 | 0.7 |

EXAMPLE 4

Rosa was multiplied from nodal sections on a gel medium which was similar to that described in Example 1 except that it contained 1 mg per litre benzylaminopurine and 0.1 mg per litre naphthyleneacetic acid. In addition, the vitamin and amino acid constituents of Murashige and Skoog (1962) formulation were substituted by the following formulation:

| | |
|---|---|
| Glycine | 1 mg/l |
| biotin | 0.05 mg/l |
| myo-inositol | 100 mg/l |
| nicotinic acid | 5 mg/l |
| pyroxidine.HCl | 0.5 mg/l |
| thiamine.HCl | 0.5 mg/l |
| folic acid | 0.5 mg/l |

The multiplication medium was solidified using 8 g/l agar.

The preparation of plants for experimental observation was carried out in two stages:

(i) Nodal sections were taken, and, in order to stimulate development of axillary buds, were first cultured in vitro for 1 week in a gel medium which was similar to the multiplication medium described above, except that paclobutrazol was added at the levels of 0.5 and 1 mg per litre.

(ii) Each propagated portion was then transferred intact to a liquid rooting medium where they were placed on 10 mm porous carriers ("Sorbarod") housed in vitro. The rooting medium was similar to the multiplication medium and contained the corresponding levels of paclobutrazol. However, the vitamin and amino acid supplement was included at only half strength and benzylaminopurine and agar were excluded.

In vitro cultures were maintained under the physical conditions described in Example 2, and 30 replicate batches of plantlets were cultured in each case. The batches containing paclobutrazol were compared with a control 30 replicate batch, which was treated in exact manner, but contained no paclobutrazol.

After 4 weeks in the rooting medium, the plantlets were then potted up and transferred to an in vivo growth room as described in Example 2. Little initial wilting was observed, but wilting was assessed after 24 hours using the to 5 score described in Example 2. The results are presented in Table 4 as a mean of the 30 replicates.

Roses are less hardy than are chrysanthemum and a number of plants failed to survive the transfer to in vivo conditions. The number of viable plants in each 30 replicate batch was determined 5 days after transfer and the results are expressed in percentage terms in Table 4.

WILTING AND SURVIVAL OF MICROPROPAGATED
ROSES FOLLOWING TRANSPLANTATION

| In Vitro Medium | Wilting one day after transplantation | Survival (%) |
|---|---|---|
| Porous carrier/ paclobutrazol (1 mg per liter) | 2.3 | 57 |
| Porous carrier/ paclobutrazol (0.5 mg per liter) | 2.4 | 37 |
| Porous carrier/ No paclobutrazol | 3.1 | 17 |
| Agar | 3.5 | 23 |

I claim:

1. A process for improving the viability of plantlets on transfer from in vitro micropropagation conditions to in vivo conditions which comprises incorporating in the in vitro medium from 0.001 to 10 mg of a plant growth regulator per litre of in vitro medium wherein the plant growth regulator is 1-(4-chlorophenyl)-4,4-dimethyl-2-(1H-1,2,4-triazol-1-yl)pentan-3-ol and stereoisomers thereof.

2. A process for improving the viability of plantlets on transfer from in vitro micropropagation conditions to in vivo conditions which comprises culturing the plantlets in contact with a solid porous carrier housed in vitro in a liquid in vitro culture medium wherein there is incorporated in the in vitro medium from 0.001 to 10 mg of a plant growth regulator per litre of in vitro medium and wherein the plant growth regulator is 1-(4-chlorophenyl)-4,4-dimethyl-2-(1H-1,2,4-triazol-1-yl)pentan-3-ol and stereoisomers thereof.

3. A process according to claim 2 wherein the solid porous carrier is a plug of fibrous material.

4. A process according to claim 3 wherein the fibrous material is cellulose.

5. A process according to claim 1 wherein there is applied to the in vitro medium from 0.05 to 5 mg of plant growth regulator per litre of in vitro medium.

6. A process according to claim 1 wherein there is applied to the in vitro medium from 0.1 to 1 mg of plant growth regulator per litre of in vitro medium.

7. A process according to claim 1 wherein the plant growth regulator is paclobutrazol.

* * * * *